US006495341B1

(12) United States Patent
Zenhausern (10) Patent No.: US 6,495,341 B1
(45) Date of Patent: Dec. 17, 2002

(54) METHOD AND APPARATUS FOR MONITORING A PHYSICAL OR CHEMICAL CONVERSION OF A GRAIN MATERIAL

(75) Inventor: Frederic Zenhausern, Fountain Hills, AZ (US)

(73) Assignee: Alpha MOS (FR)

( * ) Notice: Subject to any disclaimer, the term of this patent is extended or adjusted under 35 U.S.C. 154(b) by 0 days.

(21) Appl. No.: 09/687,407

(22) Filed: Dec. 28, 2000

Related U.S. Application Data
(60) Provisional application No. 60/159,148, filed on Oct. 13, 1999.

(51) Int. Cl.[7] .............................................. G01N 33/04
(52) U.S. Cl. ..................... 435/31; 435/287.5; 435/29; 435/34; 436/122; 436/20
(58) Field of Search .................. 99/487; 435/287.5, 435/34; 422/79, 78, 84, 89; 436/62, 20; 73/23.2

(56) References Cited

U.S. PATENT DOCUMENTS

| | | | |
|---|---|---|---|
| 5,598,770 A | * | 2/1997 | Campbell et al. .............. 99/487 |
| 6,063,617 A | * | 5/2000 | Young et al. ................ 435/287 |
| 6,244,096 B1 | * | 6/2001 | Lewis et al. .................. 73/23.2 |

* cited by examiner

Primary Examiner—Jill Warden
Assistant Examiner—Sam P Siefke
(74) Attorney, Agent, or Firm—Mathews, Collins, Shepherd & McKay, P.A.

(57) ABSTRACT

The present invention is a method and apparatus for monitoring, preferably in real time, the physical or chemical conversion of a grain material. The method employs multivariate analysis of a collected sample. In a preferred embodiment a steeping conversion is monitored by multicomponent chemical analysis of the steepwater.

16 Claims, 8 Drawing Sheets

METHOD AND APPARATUS FOR MONITORING A PHYSICAL OR CHEMICAL CONVERSION OF A GRAIN MATERIAL

CROSS REFERENCE TO RELATED APPLICATIONS

This application claims the benefit of U.S. Provisional application, Ser. No. 60/159,148 filed by the present inventor on Oct. 13, 1999 and entitled "Method and Apparatus For Monitoring At Least One Of A Physical Or Chemical Conversion Of A Grain Material," which is incorporated herein by reference. This application is related to U.S. patent application Ser. No. 09/332,659 filed Jun. 14, 1999, and U.S. patent application Ser. No. 09/407,581 filed Sep. 28, 1999, which were filed by the present inventor, assigned to the present assignee and both of which are incorporated herein by reference.

FIELD OF THE INVENTION

This invention relates to a method and apparatus for monitoring selection, production and quality of products, coproducts and byproducts converted from grain material preferably during wet milling.

BACKGROUND OF THE INVENTION

The ability to monitor the processing of grain material is increasingly important in the grain milling and ethanol industries. Traditionally, mills accommodate various productions that often use similar processes and products. For example, some wet milling processes may be suited for ethanol or fructose production, and they can also be used for starch production. Today, the industry is focussing on integrating processes with product lines and increased product potential. Monitoring permits enhanced control of the distribution of products converted.

One preferred application of the present invention is monitoring the wet milling process used to separate corn into its four basic components: starch, germ, fiber and protein. There are five basic steps to this process. First the incoming corn is inspected and cleaned. Then it is steeped for 30 to 40 hours to begin breaking the starch and protein bonds. Next the product is coarsely ground to separate the germ from the rest of the kernel. The remaining slurry consisting of fiber, starch and protein is finely ground and screened to separate the fiber from the starch and protein. The starch is typically separated in hydrocyclone compounds. Then the starch can be converted to syrup or be fermented into other products.

The steeping equipment typically comprises a stainless steep tank which can hold about 3000 bushels of corn for 30 to 40 hours of soaking in 50 C water. During steeping, the kernels absorb water, increasing their moisture levels typically from 15% to 45%, and more than double their size. The addition of about 0.1% sulfur dioxide to the water prevents excessive bacterial growth in the warm environment. As the corn swells and softens, the mild acidity of the steepwater begins to loosen gluten bonds within the corn and to release starch. After steeping, the corn is coarsely ground to break the germ loose from other components. Steepwater is condensed to capture nutrients in the water for use in animal feeds and for use as a nutrient in later fermentation processes. The ground corn, in a water slurry, flows to a germ separator. Then, the process may comprise additional steps such as germ separation, fine grinding and screening, starch separation, syrup conversion and fermentation.

Although the chemical and biochemical reactions involved in corn wet-milling are still not fully understood, many engineering processes have been developed to facilitate wet-milling. One example is the counter-current steeping method described in Wet milling in Technology of Corn Wet-Milling and Associated Processes, 69–125, ed. P. H. Blanchard, London, England, Elesevier Sci. Pub, 1992. Several studies of the steeping process have been reported in the literature. See, for example, Steinke J. D. et al., "Steeping maize in the presence of multiple enzymes," *Cereal Chem.*, 68(1), 12–17, 1991; Yaptenco K. F. et al., "A laboratory countercurrent steep battery for corn wet-milling," *Cereal Chem.*, 73(2), 249–256, 1996 and Yang P. et al., "A laboratory-scale continuous countercurrent steep system for corn wet-milling", *Transactions of ASAE*, 41(3), 721–726, 1998. All of the patents, articles and references set forth in this "Background of the Invention" are incorporated herein by reference.

SUMMARY OF THE INVENTION

The present invention is a method and apparatus for monitoring, preferably in real time, the physical or chemical conversion of a grain material. The method employs multivariate analysis of a sample from the converted product. In a preferred embodiment a steeping conversion is monitored by multicomponent chemical analysis of the steepwater.

BRIEF DESCRIPTION OF THE DRAWINGS

The advantages, nature and various additional features of the invention will appear more fully upon consideration of the illustrative embodiments now to be described in detail in connection with the accompanying drawings. In the drawings:

FIGS. 3–9 are graphical illustrations useful in understanding a specific example of the invention.

DETAILED DESCRIPTION OF THE INVENTION

In essence, the invention is a method for analyzing a conversion (chemical or physical) of a grain material comprising processing the grain material to undergo the conversion to a converted product, sampling the converted product, exposing the sample to a sensing probe to produce an output signal and analyzing the output signal using multivariate analysis to determine a plurality of component levels indicative of the degree of conversion of the grain material. In a preferred application, the method can map various components of a liquid medium, preferably steepwater from a wet milling process, and detect (and possibly predict) the presence of solids, contaminants, lactic acid products and byproducts and sulfur oxides. It can also detect minute quantities of organic and solvent molecules or interfering components which can be correlated with conversion of the grain material.

Figure 1:
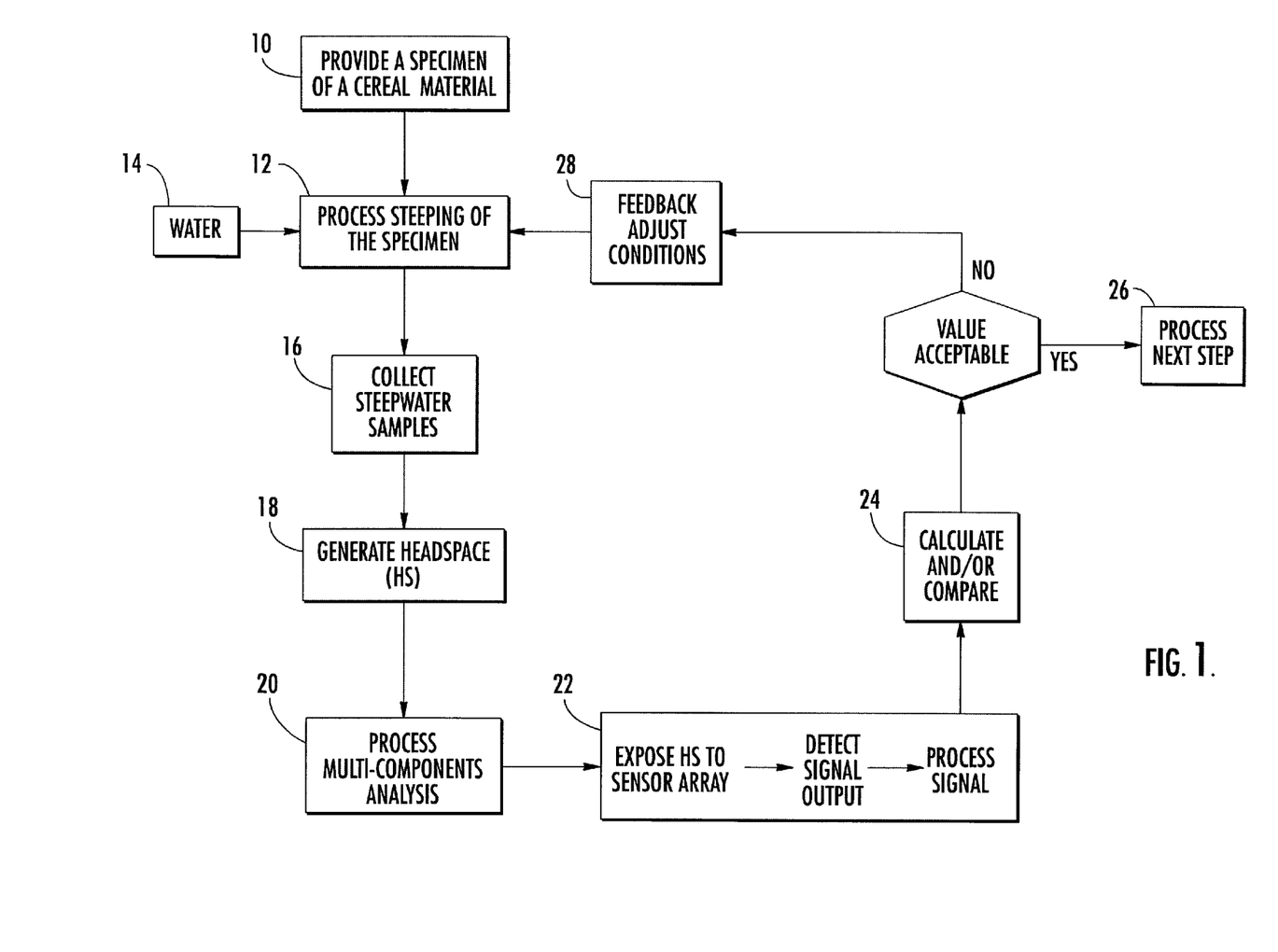
FIG. 1 is a schematic flow diagram of an exemplary method in accordance with the invention.

Referring to the drawings, FIG. 1 is a schematic flow diagram of an exemplary method in accordance with the invention. The first step is steeping a grain material to produce a converted product. This involves providing a quantity of a grain material (preferably a cereal material such as corn) as illustrated in block 10 of FIG. 1. Water is added to the material as shown in Block 14, and the material can be steeped in the conventional manner as described hereinabove (Block 12).

The next step is to sample the converted product. This advantageously is done by collecting one or more steepwater samples (Block 16). Advantageously headspace may be generated in the steepwater sample(s) to provide a gas sample for analysis. (Block 18).

The third step illustrated in Blocks 20, 22 is to expose the sample to one or more sensing probes to produce an output signal reflecting at least one physical or chemical change in the sample and, using multivariate analysis, to analyze the output signal to determine component levels such as $SO_2$ concentration, pH value, acidity and total solids content. The multivariate analysis is advantageously carried out by a computer (not shown in FIG. 1).

Any of a wide variety of conventional sensors can be used. The preferred sensor probe is a gas sensor array comprising a plurality of different metal oxide sensors to provide a multivariable output signal subject to multivariate analysis. The output variables advantageously correspond to physical, chemical or other parameters characteristic of the converted product or components thereof. several useful alternative sensors have been described in the art. In particular, arrays of semiconductor sensors having sensitive and chemically-diverse interface materials capable of interacting with analytes of complex mixtures can be used. These can incorporate many operating principles including: doped tin-oxide gas sensors, doped conductive polymers, field effect transistor (FET) devices, and optical fiber devices.

The sensors can be based on specific chemical adsorption. For example, selective coatings or other surface modifications can be added to sensors such as immunoFET's, redox enzyme electrodes, ion-channel simulating devices or coated piezoelectric or surface acoustic wave devices. See Gardner J. W. et al., *Sensor Actuators*, B18–19, 211–220, 1994. Recently, mass sensing quadrupole transducers using mass spectrometers have become commercially available for the application in food quality control. Such sensors can analyze sample headspace. See U.S. Pat. No. 5,363,707 to Augenblick et al.

Other useful sensors include (i) resonant microstructures (see U.S. Pat. No. 5,025,346 to Tang et al.; U.S. Pat. No. 5,445,008 to Wachter et al., and Thomas et al., *Rev. Sci. Instrum.*, 65(12), 3793–98, 1994), (ii) amperometric, conductivity/capacitance sensing platforms (see U.S. Pat. No. 5,801,297 to Mifsud et al.) and (iii) optical detectors (see U.S. Pat. No. 5,563,707 to Werner et al.; U.S. Pat. No. 5,512,490 to Walt et al.; U.S. Pat. No. 5,004,914 to Vali et al.; U.S. Pat. No. 5,436,167 to Robillard and U.S. Pat. No. 5,015,843 to Seitz et al.

Advantageous sensors are described by Dickinson et al. in *Nature*, 382, 697–700, Aug. 22, 1996. These sensors employ a miniaturized array of fibers containing a special fluorescent dye (Nile Red) embedded in a polymer matrix. The dye exhibits large wavelength shifts in its strong fluorescent response to various vapors. The dye is photochemically stable and can be immobilized in the polymers. A sensor array uses nineteen 300 $\mu$m optical fibers with their flat sensing ends coated with the dye encapsulated in various polymers. A video frame grabber permits fluorescent intensity versus time data to be recorded. From the variations in response time and the individual fiber light outputs, the system can be trained to identify specific vapors. To some extent photobleaching of the dye molecules limits the reliability and reproducibility of the sensor system.

Gas sensors, developed for the detection toxic substances and odiferous substances, can be used for microorganism detection in the manner described by Payne et al. in U.S. Pat. No. 5,807,701. The Payne et al. sensor uses an array of conducting polymer gas sensors to sample vapor associated with the microorganisms.

Any one of several techniques can be used to perform the multivariate analysis of the sensor output(s). The preferred analysis is the use of a principal component algorithm.

By way of background, multicomponent mixtures such as solutions, gases, solids, process streams, effluents, and contents of reaction chambers usually have many variables that interact with each other. For example, absorbance peaks of several components can overlap each other. These variables should be analyzed simultaneously to optimize the useful analytical data that would be obscure in traditional analytical techniques.

Multicomponent mixtures can be analyzed by a multivariate analysis based on the reference data. See H. M. Heise et al., "Multivariate calibration for near-infrared spectroscopic assays of blood substrates in human plasma based on variable selection using partial least squares (PLS) regression vector choices", *Fresenius' Journal of Analytical Chemistry*, 362(1) (1998) 141–147. Nonlinear multivariate calibration methods have been reviewed in Sekulic et al. *Analytical Chemistry*, 65 (1993) 835A–845A.

Other alternative multivariate analysis techniques include artificial intelligence techniques such as artificial neural networks (ANN), expert systems (ESs), fuzzy logic (FL), and genetic algorithms (GAs). ANNs learn by training. ESs are based on defined rules. FL systems are based on uncertainty and partial truths. These techniques can be used in concert. A family of new techniques using probabilistic indexing algorithms such as Fast Look-up Algorithm for String Homology (FLASH), hash algorithms, and data mining algorithms are described in U.S. Pat. No. 5,752,019 issued to Ligoutsas. Bayes algorithms (also called Bayesian statistical methods) are described in Stolory et al., "Predicting Protein Secondary Structure Using Neural Net and Statistical Methods" *J. Mol. Biol.* 225 (1992) 363.

There are also the factor-based or bilinear projection methods of PLS, sometimes called Projection to Latent Structures, Principal Components Analysis (PCA), and Principle Components Regression (PCR). PLS is a good technique for process control when both process and product data are used to control the process. See Stone et al., "Continuum Regression: Cross-validated Sequentially Constructed Prediction Embracing Ordinary Least Squares, Partial Least Squares and Principal Components Regression," *Journal of the Royal Statistical Society B*, 52, 237–269, (1990). Nonlinear Principle Components Regression (NLPCR) and Nonlinear Partial Least Squares (NLPLS) can model nonlinear responses. See Sekulic et al., *Analytical Chemistry*, 65 (1993) 835A–845A. Soft Independent Modeling of Class Analogy (SIMCA) is another suitable multivariate method. The results of the multivariate analysis are usually used directly to give concentration values for the measured analyte.

The effect of the multivariate analysis is to reconstruct analytical data from several variables. The multivariate process monitoring handles noise and drift better, with fewer false alarms, than univariate monitoring. For example, the multivariate analysis can determine an analyte's concentration from several of its absorbance peaks. Multivariate analysis can be applied to most analytical and process control techniques including fluorescence, chromatography, absorption spectroscopy, emission spectroscopy, X-ray methods, radiochemical methods, nuclear magnetic resonance spectroscopy, electron spin resonance spectroscopy, surface science techniques, refractometry, interferometry, mass spectrometry, gas density, magnetic susceptibility, electrochemistry, surface acoustic wave sensors, sensor arrays, ultrasonic sensors, and thermal analysis.

Multiple variables can be converted into useful analytical data by multivariate analysis. Thus multivariate analysis or multivariate technique can relate instrumental response to the concentrations, physical, chemical, or physico-chemical properties at several wavelengths.

An advantageous additional step (Blocks 24, 28) is to ascertain whether the component levels are acceptable for the conversion (steeping) and, if not, to adjust the conditions of the conversion (steeping) process.

The following example will serve to further typify the nature of this invention but should not be construed as a limitation in the scope thereof.

EXAMPLE

Figure 2:
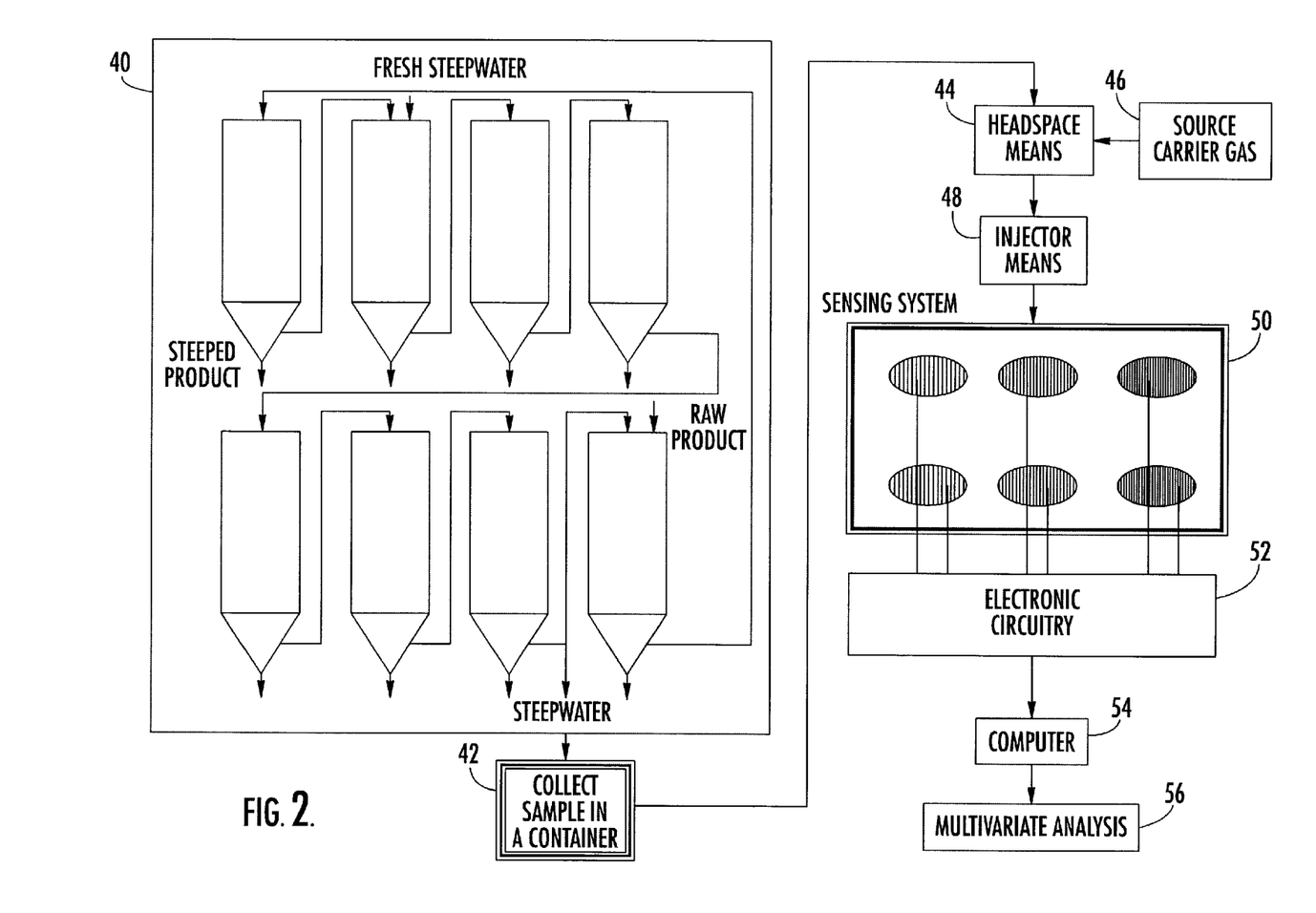
FIG. 2 is a schematic diagram of exemplary apparatus for practicing the method of FIG. 1.

Referring to FIG. 2, steepwater samples 42 from several different steeping tanks 40 were analyzed by using a commercially available gas sensor array system 50 (e.g. Prometheus system including mass spectrometer and 12 different metal oxide sensors, Alpha-MOS, New Jersey, USA) equipped with a headspace autosampler 44, 46 (HS100 CTC, Switzerland) and an air conditioning unit (not shown) (ACU500, Alpha-MOS, New Jersey, USA) (not shown). About 5 ml of the steepwater samples were directly disposed into 10 ml glass vials hermetically sealed with septum caps. The vials were loaded onto a tray of the headspace autosampler for which the following parameters were set; 20 minutes of incubation time in oven at 45 C with 500 rpm agitation speed, 4.5 ml headspace capture for injection at 1 microliter per second into the gas sensing analyzer and 2 minutes flushing of the gas syringe with air (e.g. zero air quality). The sensor acquisition time was set at 2 minutes with an acquisition period of 0.5 second while a delay of 8 minutes was set between consecutive injection. The gas flow rate was typically set at 150 ml/min. In practice, the parameters for mass spectrometry analysis were exploiting similar headspace conditions. Typically, the instrument (50, 52, 54) was used in a scan mode ranging masses from 30 to 150 amu within 120 s and with about 40 scans and an accuracy about 10 keeping the scan time below approximately 3 second.

Figure 3:
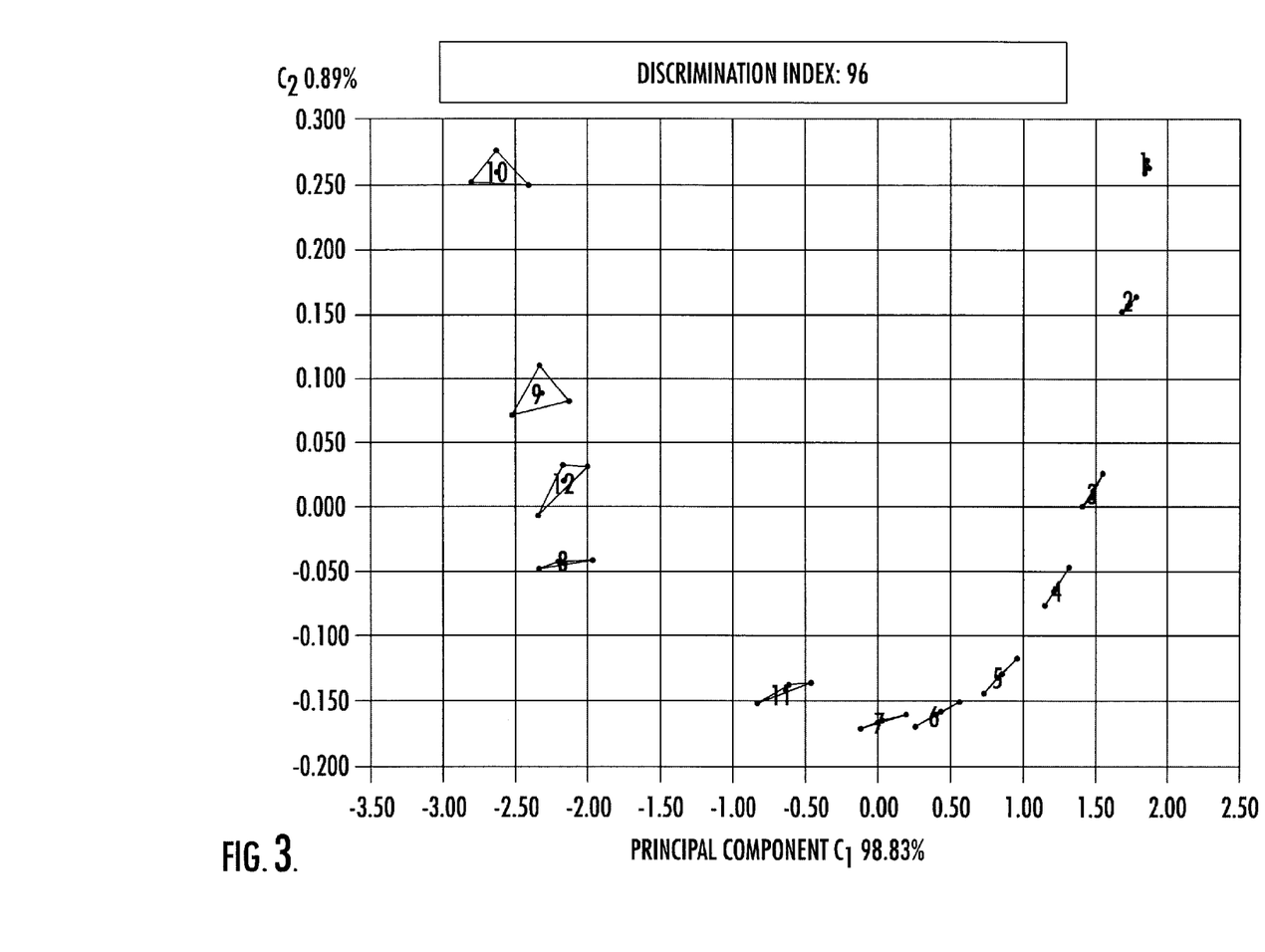

FIGS. 3–9 are associated graphical illustrations. FIG. 3 is a two-dimensional plot of a typical multivariate analysis output using a principal component algorithm. It exhibits a dilution effect (i.e. a "bell shaped" curve between different clusters). Such effects can be quantitatively measured with preferably a Partial Least Squares (PLS) algorithm providing a good correlation (>80%) between, for example, the concentrations of sulfur dioxide (10–2000 ppm) and total solids or protein content (0–3%). This illustrates the usefulness of the method for monitoring the steeping process.

Figure 4:
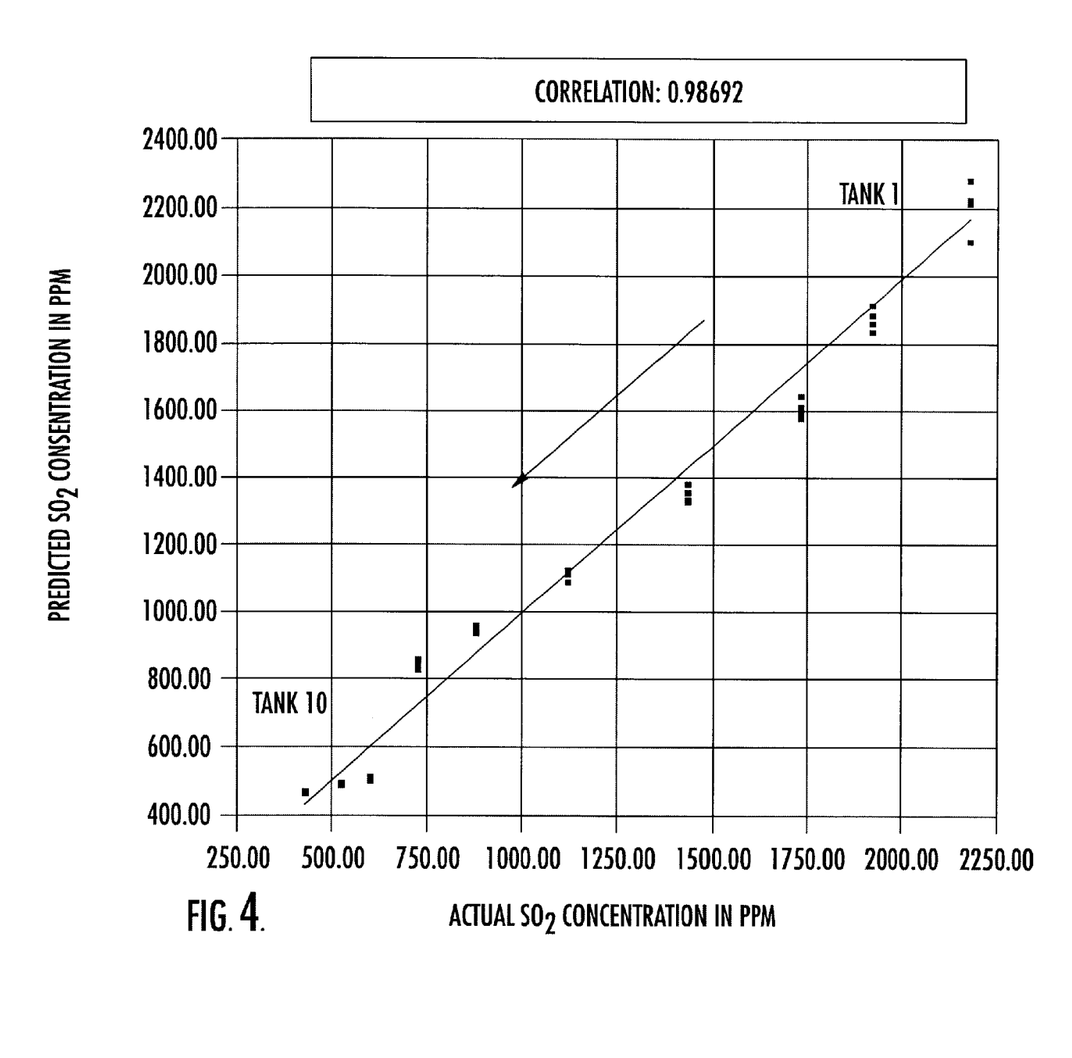
Figure 5:
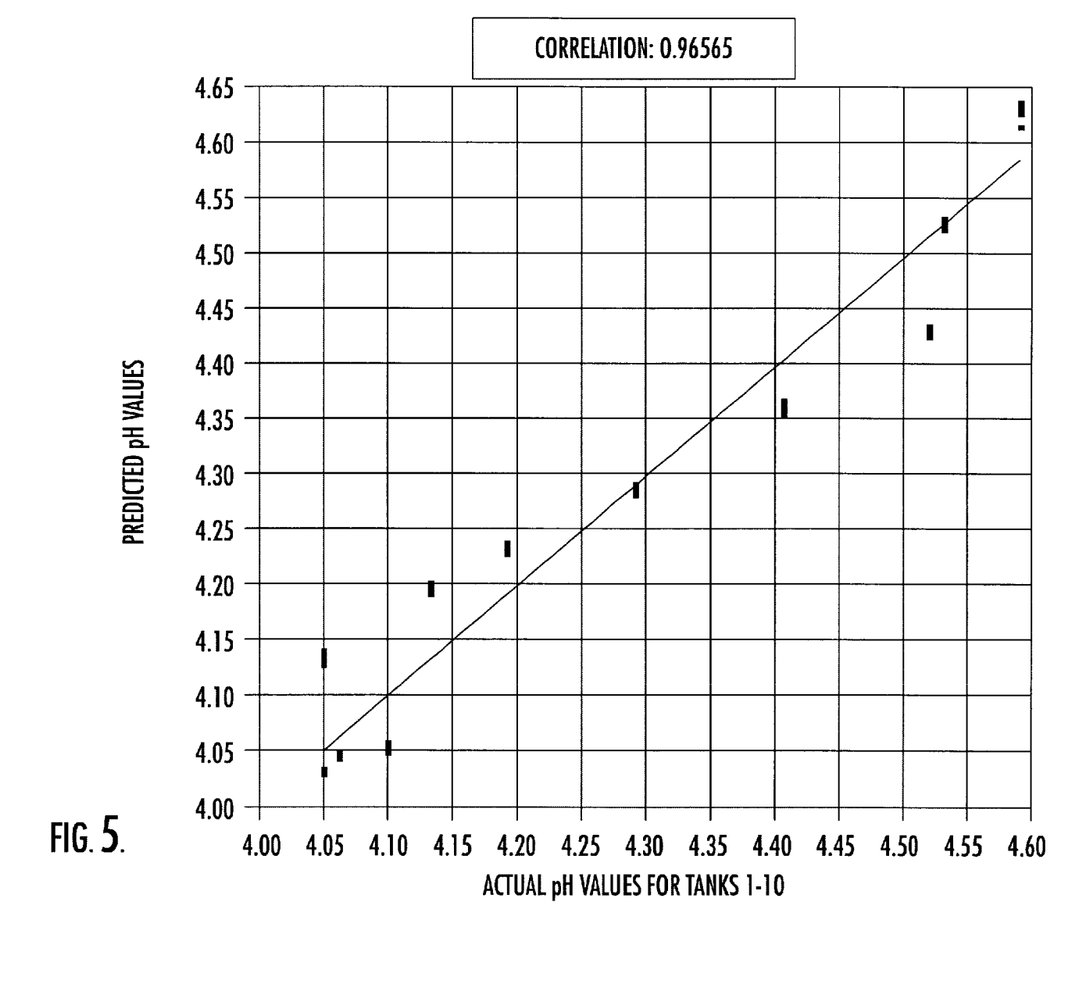
Figure 6:
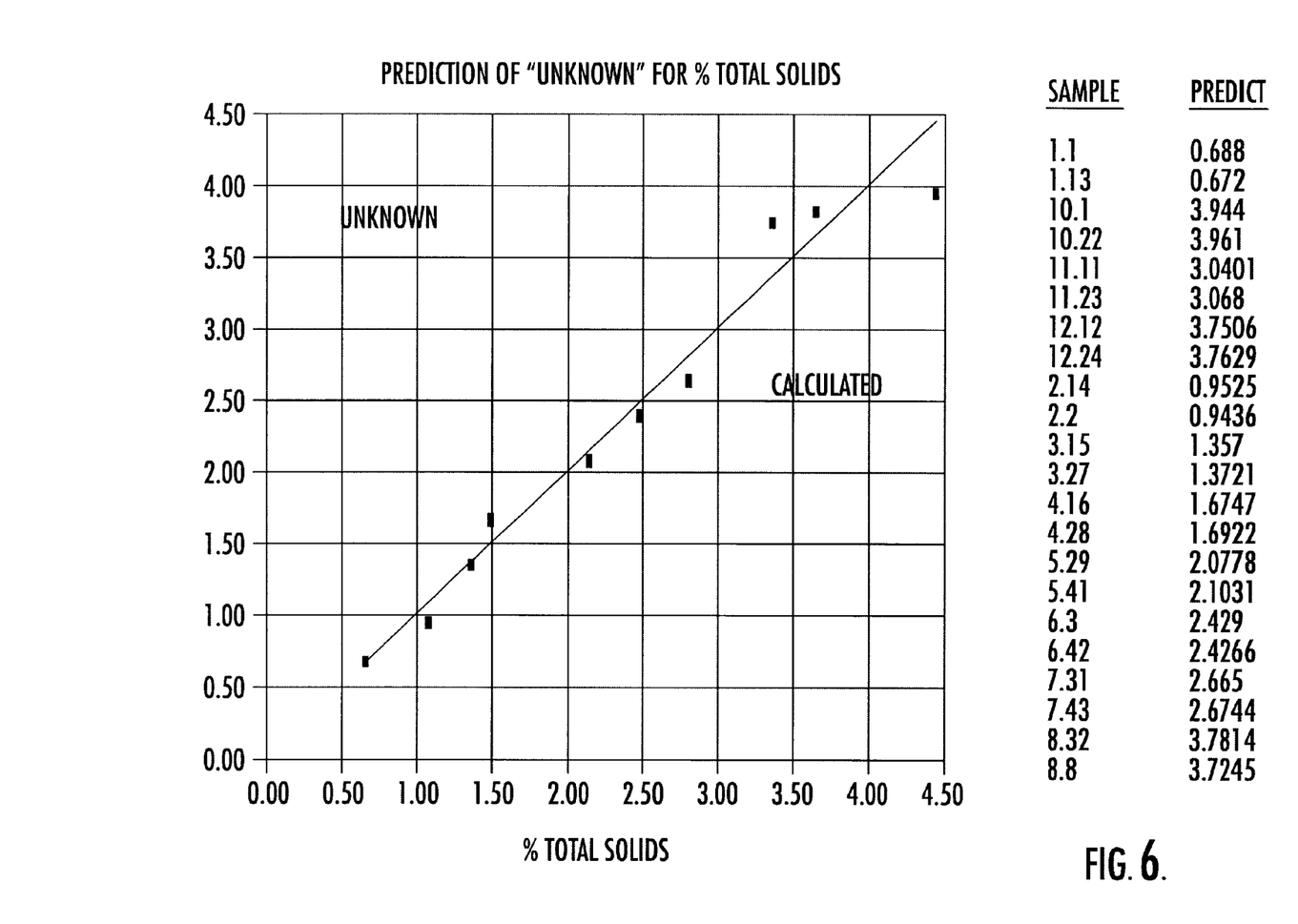
Figure 7A:
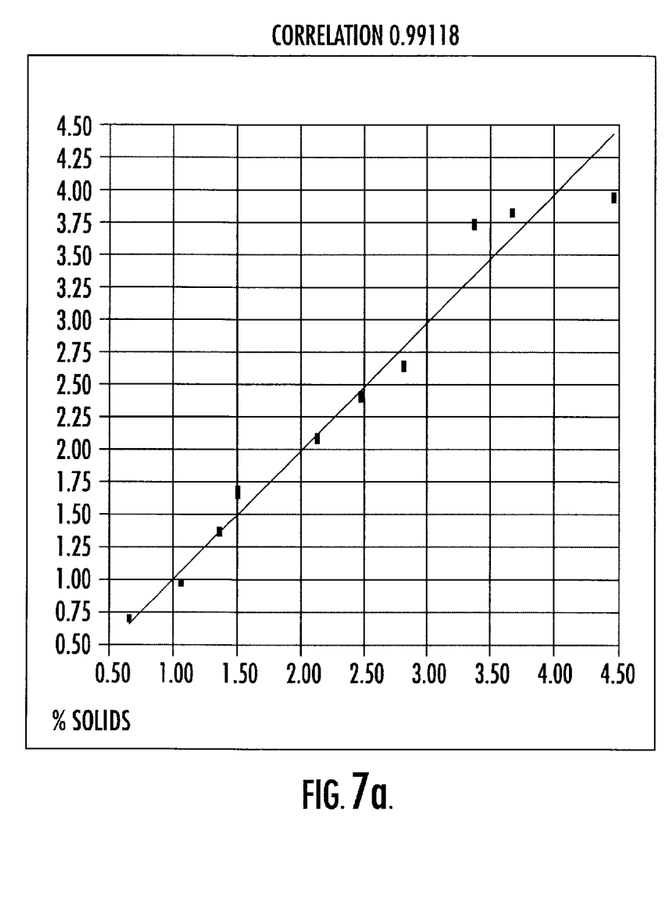
Figure 7B:
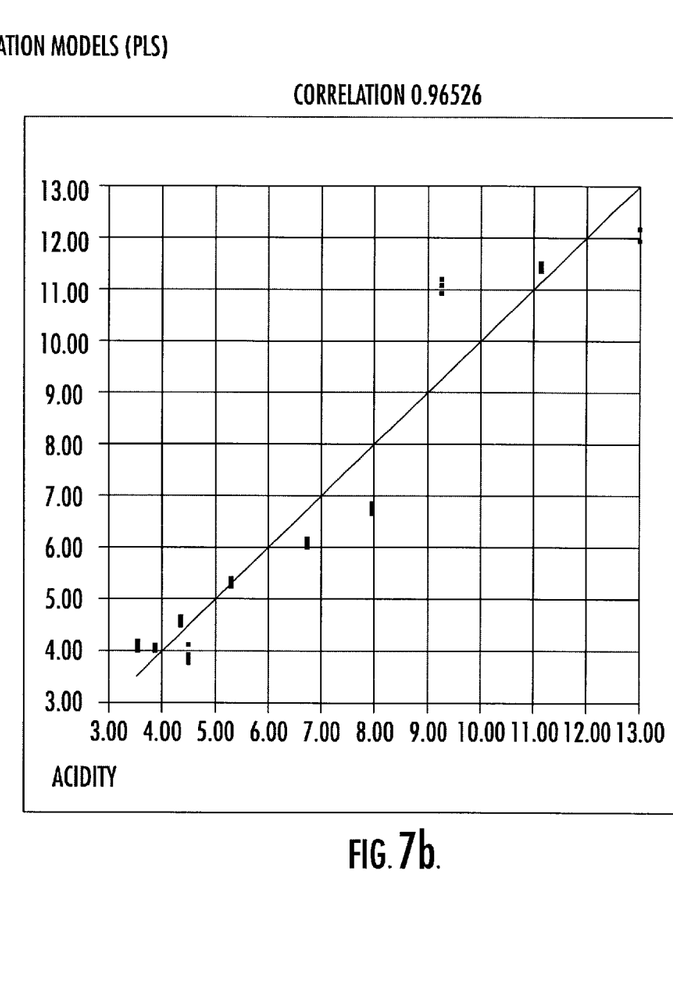
Figure 8:
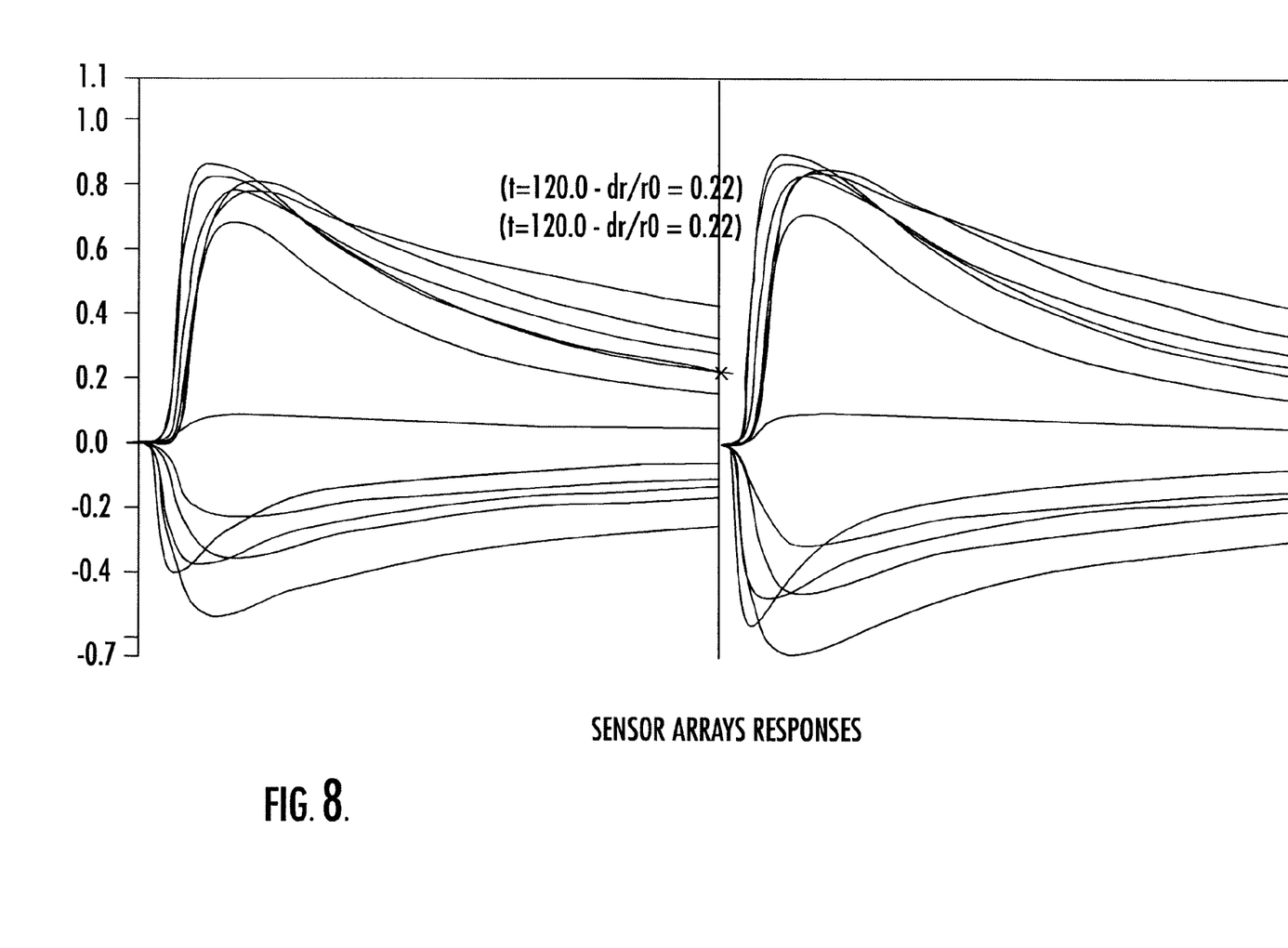

The steepwater profiles are shown in the FIGS. 4–6 where the discrimination of different samples can be discriminated and/or classified. FIGS. 4 and 5 show a graphical model with a prediction score of an unknown sample using a Partial Least Squares (PLS) algorithm to predict the concentration of sulfur dioxide and the pH values, respectfully, in the steepwater samples. FIG. 6 shows a graphical model with a prediction score of an unknown sample using a PLS algorithm to predict the content in solids (protein) in steepwater samples. FIG. 7 displays plots for the percentage in solid and acidity values obtained during multi-component analysis using the method and apparatus of the invention. The model was built using a PLS algorithm. FIG. 8 is a plot of the sensor for which the resistance ratio $\Delta R/Ro$ is a function of time, and FIG. 9 is a plot displaying normalized intensity values for different masses obtained by mass quadrupole spectrometry.

It is to be understood that the above-described embodiments are illustrative of only a few of the many possible specific embodiments which can represent applications of the principles of the invention. Numerous and varied other arrangements can be readily devised by those skilled in the art without departing from the spirit and scope of the invention.

What is claimed is:

1. A method for analyzing a physical or chemical conversion of a grain material comprising the steps of:

processing a grain material to undergo a physical or chemical conversion to a sample, the sample comprising a converted product and optionally one or more of aqueous, gaseous or solid components;

sampling the converted product and/or at least one of the aqueous, gaseous, or solid components;

exposing the sample to at least one sensing probe to produce an output signal; and analyzing the output signal by multivariate analysis to determine at least one component level indicative of the degree of physical or chemical conversion of the grain material, wherein a component of the converted product is a micro-organism.

2. A method for analyzing a physical or chemical conversion of a grain material comprising the steps of:

steeping the grain material to produce a sample, the sample comprising a steeped product and optionally one or more of aqueous, gaseous or solid components;

sampling the steeped product and/or at least one of the aqueous gaseous, or solid components, exposing the sample to at least one sensing probe to produce an output signal; and analyzing the output signal by multivariate analysis to determine one or more component levels from the group consisting of $SO_2$ concentration, pH value, and total solids content, wherein a component of the converted product is a micro-organism.

3. The method of claim 2 further comprising the step of ascertaining whether the component levels are acceptable for the steeping process and optionally adjusting the conditions of the steeping process in response to the step of ascertaining.

4. The method of claim 2 wherein the step of sampling comprises generating a headspace to produce a gas phase and wherein said step of exposing comprises exposing the gas phase to the at least one sensing probe.

5. An apparatus for analyzing a physical or chemical conversion of a grain material, said apparatus comprising:

means for processing a grain material to undergo a physical or chemical conversion to a sample, the sample comprising a converted product and optionally one or more of aqueous, gaseous or solid components;

a sensing probe exposed to the sample of the converted product and/or least one of the gaseous, or solid components to produce an output signal; and a computer responsive to the output signal to analyze the output signal by multivariate analysis to determine one or more component levels in the converted product indicative of the degree of physical or chemical conversion of the grain material, wherein a component of the converted product is a micro-organism.

6. The apparatus of claim 5 wherein the sample comprises at least a grain material.

7. The apparatus of claim 5 wherein the means for processing a grain material comprises a container for receiving said sample and can accommodate a multi-component mixture for converting the grain material using a steeping process.

8. The apparatus of claim 5 wherein the means for processing the grain material includes a steepwater tank.

9. The apparatus of claim 5 wherein the grain material is corn.

10. The apparatus according to claim 5 wherein the mixture comprises an aqueous solution.

11. The apparatus according to claim 5 wherein said component levels are selected from the group consisting of $SO_2$ concentration, pH value, acidity, and total solids content.

12. An apparatus for analyzing a physical or chemical conversion of a grain material, said apparatus comprising:
   means for processing a grain material to undergo a physical or chemical conversion to a sample, the sample comprising a converted product and optionally one or more of aqueous, gaseous or solid components;
   a sensing probe exposed to the sample of the converted product and/or at least one of the aqueous, gaseous, or solid components to produce an output signal; and
   a computer responsive to the output signal to analyze the output signal by multivariate analysis to determine one or more component levels in the converted product indicative of the degree of physical or chemical conversion of the grain material,
   wherein the sensing probe comprises a gas sensor array comprising a plurality of different metal oxide sensors.

13. An apparatus for analyzing a physical or chemical conversion of a grain material, said apparatus comprising:
   means for processing a grain material to undergo a physical or chemical conversion to a sample, the sample comprising a converted product and optionally one or more of aqueous, gaseous or solid components;
   a sensing probe exposed to the sample of the converted product and/or at least one of the aqueous, gaseous, or solid components to produce an output signal; and
   a computer responsive to the output signal to analyte the output signal by multivariate analysis to determine one or more component levels in the converted product indicative of the degree of physical or chemical conversion of the grain material,
   wherein the sensing probe comprises an array of semiconductor sensors having sensitive and chemically-diverse interface material capable of interacting with analytes in complex mixtures.

14. The apparatus of claim 13 wherein the sensing probe is selected from the group consisting of doped tin-oxide gas sensors, doped conductive polymers, field effect transistor devices, and optical fiber devices.

15. An apparatus for analyzing a physical or chemical conversion of a grain material, said apparatus comprising:
   means for processing a grain material to undergo a physical or chemical conversion to a sample, the sample comprising a converted product and optionally one or more of aqueous, gaseous or solid components;
   a sensing probe exposed to the sample of the converted product and/or at least one of the aqueous, gaseous, or solid components to produce an output signal;
   a computer responsive to the output signal to analyze the output signal by multivariate analysis to determine one or more component levels in the converted product indicative of the degree of physical or chemical conversion of the grain material,
   wherein the sensing probe comprises a mass sensing quadrupole transducer.

16. An apparatus for analyzing a physical or chemical conversion of a grain material, said apparatus comprising:
   means for processing a grain material to undergo a physical or chemical conversion to a sample, the sample comprising a converted product and optionally one or more of aqueous, gaseous or solid components;
   a sensing probe exposed to the sample of the converted product and/or at least one of the aqueous, gaseous, or solid components to produce an output signal; and
   a computer responsive to the output signal to analyze the output signal multivariate analysis to determine one or more component levels in the converted product indicative of the degree of physical or chemical conversion of the grain material,
   wherein the sensing probe comprises an array of fibers, the fibers having an end coated with a fluorescent dye, the fluorescent dye undergoing a wavelength shift in response to vapors present during the physical or chemical conversion of a grain product.

* * * * *